(12) United States Patent
Burke et al.

(10) Patent No.: US 10,750,749 B2
(45) Date of Patent: *Aug. 25, 2020

(54) PROCESS AND COMPOSITION FOR KILLING SPORES

(71) Applicant: American Sterilizer Company, Mentor, OH (US)

(72) Inventors: Peter A. Burke, Concord, OH (US); Mark James Leggett, Cardiff (GB)

(73) Assignee: American Sterilizer Company, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/262,840

(22) Filed: Apr. 28, 2014

(65) Prior Publication Data

US 2015/0305342 A1 Oct. 29, 2015

(51) Int. Cl.
*A01N 59/00* (2006.01)
*A61L 2/18* (2006.01)
*A61K 45/06* (2006.01)
*A61K 33/40* (2006.01)
*A61L 2/00* (2006.01)

(52) U.S. Cl.
CPC .............. *A01N 59/00* (2013.01); *A61K 33/40* (2013.01); *A61K 45/06* (2013.01); *A61L 2/186* (2013.01); *A61L 2/0088* (2013.01); *A61L 2202/24* (2013.01)

(58) Field of Classification Search
None
See application file for complete search history.

(56) References Cited

U.S. PATENT DOCUMENTS

| | | | | |
|---|---|---|---|---|
| 3,786,615 A | | 1/1974 | Bauer | |
| 3,872,038 A | * | 3/1975 | Adams | B29C 33/64 106/38.22 |
| 4,051,058 A | | 9/1977 | Bowing | |
| 4,051,059 A | | 9/1977 | Bowing | |
| 4,269,602 A | * | 5/1981 | Worth | D06M 11/82 252/8.61 |
| 4,323,467 A | * | 4/1982 | Fu | A61L 12/08 134/42 |
| 4,415,682 A | * | 11/1983 | Becker | C08G 59/182 523/402 |
| 4,731,222 A | | 3/1988 | Kralovic et al. | |
| 4,743,447 A | * | 5/1988 | Le Rouzic | A01N 59/00 424/616 |
| 4,892,706 A | | 1/1990 | Kralovic et al. | |
| 4,896,768 A | | 1/1990 | Anderson | |
| 4,910,014 A | * | 3/1990 | Nakagawa | A61K 8/29 424/49 |
| 4,996,048 A | * | 2/1991 | Bhagwat | A01N 59/12 422/37 |
| 5,190,724 A | | 3/1993 | Hachmann | |
| 5,437,868 A | | 8/1995 | Oakes | |
| 5,508,046 A | * | 4/1996 | Cosentino | A01N 59/00 424/616 |
| 5,527,508 A | | 6/1996 | Childers et al. | |
| 5,545,343 A | * | 8/1996 | Brougham | A01N 37/16 252/186.26 |
| 5,656,302 A | * | 8/1997 | Cosentino et al. | 424/616 |
| 5,767,163 A | | 6/1998 | Kundsin | |
| 5,770,232 A | | 6/1998 | Sizer | |
| 5,807,264 A | * | 9/1998 | Paltieli | A61B 5/411 600/477 |
| 5,851,483 A | * | 12/1998 | Nicolle | A01N 59/00 422/28 |
| 5,900,256 A | * | 5/1999 | Scoville et al. | 424/616 |
| 6,168,808 B1 | * | 1/2001 | Hamon Godin | A01N 37/16 424/126 |
| 6,224,827 B1 | | 5/2001 | Lembke | |
| 6,305,531 B1 | | 10/2001 | Wilkman | |
| 6,326,032 B1 | | 12/2001 | Richter | |
| 6,346,279 B1 | | 2/2002 | Rochon | |
| 6,387,858 B1 | * | 5/2002 | Shah | C11D 3/222 510/161 |
| 6,448,062 B1 | * | 9/2002 | Huth et al. | 435/264 |

(Continued)

FOREIGN PATENT DOCUMENTS

| | | | |
|---|---|---|---|
| EP | 1252819 | 10/2002 | |
| EP | 1293215 A1 * | 3/2003 | A61L 2/18 |

(Continued)

OTHER PUBLICATIONS

Alastri et al. Canadian Journal of Microbiology 1993 (39):52-60.*
Hilgren et al. Journal of Food Protection 2009 72(2): 360-364 (Year: 2009).*
Khadre et al.; "Sporicidal action of ozone and hydrogen peroxide: a comparative study"; International Journal of Food Microbiology 71 (2001); pp. 131-138.
"Guideline for Disinfection and Sterilization in Healthcare Facilities, 2008"; Centers for Disease Control and Prevention; CDC—Disinfection & Sterilization Guideline: Disinfection—HICPAC; http://www.cdc.gov/hicpac/disinfection_sterilization/6; 6 pages, Nov. 2008.
STERIS® Product Brochure; SPOR-KLENZ® Ready to Use; Dec. 1, 2001; 3 pages.
Minntech Renal Systems; Actril® Cold Sterilant Product Brochure; Technical Notes and Research Data; Oct. 1, 1998; 12 pages.
ECOLAB; Oxonia Active Product Brochure; 2003; 2 pages.

(Continued)

*Primary Examiner* — Robert A Wax
*Assistant Examiner* — Caralynne E Helm
(74) *Attorney, Agent, or Firm* — Renner, Otto, Boisselle & Sklar, LLP

(57) ABSTRACT

This invention relates to a process and an aqueous composition for killing spores. The process comprises contacting the spores with the aqueous composition for a sufficient period of time to effect a desired reduction (e.g., at least a 4 log reduction) in the number of spores capable of reproduction, metabolism and/or growth. The aqueous composition comprises water, peracetic acid and hydrogen peroxide. The concentration of peracetic acid in the water may be in the range from about 0.001 to about 60% by weight, or from about 0.001 to about 0.5% by weight. The weight ratio of peracetic acid to hydrogen peroxide may be in the range from about 0.001 to about 0.5.

5 Claims, 1 Drawing Sheet

(56) References Cited

U.S. PATENT DOCUMENTS

| | | | |
|---|---|---|---|
| 6,589,565 B1* | 7/2003 | Richter | A01N 37/16 422/28 |
| 6,627,657 B1 | 9/2003 | Hilgren et al. | |
| 6,686,324 B2 | 2/2004 | Ramirez et al. | |
| 6,734,405 B2 | 5/2004 | Centanni et al. | |
| 6,803,057 B2 | 10/2004 | Ramirez et al. | |
| 6,906,296 B2 | 6/2005 | Centanni et al. | |
| 6,967,315 B2 | 11/2005 | Centanni et al. | |
| 7,135,142 B2 | 11/2006 | Burke et al. | |
| 7,300,638 B2 | 11/2007 | Williams et al. | |
| 7,354,604 B2 | 4/2008 | Ramirez et al. | |
| 7,435,303 B2 | 10/2008 | Biering | |
| 7,569,182 B2 | 8/2009 | Burke et al. | |
| 7,632,523 B2 | 12/2009 | Ramirez et al. | |
| 7,655,252 B2 | 2/2010 | Baker, Jr. | |
| 7,781,388 B2 | 8/2010 | Heintz | |
| 8,143,309 B2 | 3/2012 | Awad | |
| 8,470,755 B1 | 6/2013 | Tajmamet | |
| 2001/0001479 A1* | 5/2001 | Johnson et al. | 252/8.57 |
| 2003/0180377 A1 | 9/2003 | Ramirez et al. | |
| 2005/0084415 A1 | 4/2005 | McVey et al. | |
| 2006/0105930 A1* | 5/2006 | McDonnell | A01N 59/00 510/161 |
| 2006/0204467 A1 | 9/2006 | Littau | |
| 2006/0229225 A1 | 10/2006 | Martin et al. | |
| 2006/0292031 A1 | 12/2006 | Chiu | |
| 2007/0053850 A1 | 3/2007 | Tichy | |
| 2007/0264356 A1* | 11/2007 | Ames | A61L 2/186 424/616 |
| 2007/0281999 A1* | 12/2007 | Fox | A01N 31/02 514/557 |
| 2008/0045593 A1 | 2/2008 | Kaiser et al. | |
| 2008/0240978 A1 | 10/2008 | Sorensen | |
| 2009/0061017 A1 | 3/2009 | Pedersen et al. | |
| 2009/0074881 A1 | 3/2009 | Kielbania, Jr. | |
| 2009/0252775 A1 | 10/2009 | Arndt | |
| 2010/0021558 A1* | 1/2010 | Dada | A61K 33/40 424/616 |
| 2010/0108942 A1* | 5/2010 | Man | A01N 37/16 252/186.26 |
| 2012/0174872 A1 | 7/2012 | Richards | |
| 2012/0230870 A1 | 9/2012 | Franciskovich et al. | |
| 2014/0004208 A1* | 1/2014 | Golden | A01N 59/00 424/616 |
| 2015/0314025 A1* | 11/2015 | Berentsveig | A01N 37/16 424/616 |

FOREIGN PATENT DOCUMENTS

| | | | | |
|---|---|---|---|---|
| JP | | 02193905 A * | 7/1990 | A01N 37/02 |
| JP | | 7-126109 | 5/1995 | |
| JP | | 2001199811 A1 | 7/2001 | |
| WO | WO 2012075507 A2 | | 6/2012 | |
| WO | WO 2013037014 A1 | | 3/2013 | |

OTHER PUBLICATIONS

International Search Report and Written Opinion, Application No. PCT/US2015/015087, dated Apr. 30, 2015.
U.S. Appl. No. 14/538,011, filed Nov. 11, 2014.
Written Opinion of the International Preliminary Examining Authority, Application No. PCT/US2015/015087, dated Mar. 31, 2016.
International Preliminary Report on Patentability, Application No. PCT/US2015/015087, dated Jul. 14, 2016.
International Preliminary Report on Patentability, Application No. PCT/US2015/015088, dated Jun. 30, 2016.
International Preliminary Report on Patentability, Application No. PCT/US2015/015090, dated Jul. 14, 2016.
International Preliminary Report on Patentability, Application No. PCT/US2015/015091, dated Jul. 14, 2016.
Alasri et al., Canadian Journal of Micrigiology 1993 (39):52-60.

* cited by examiner

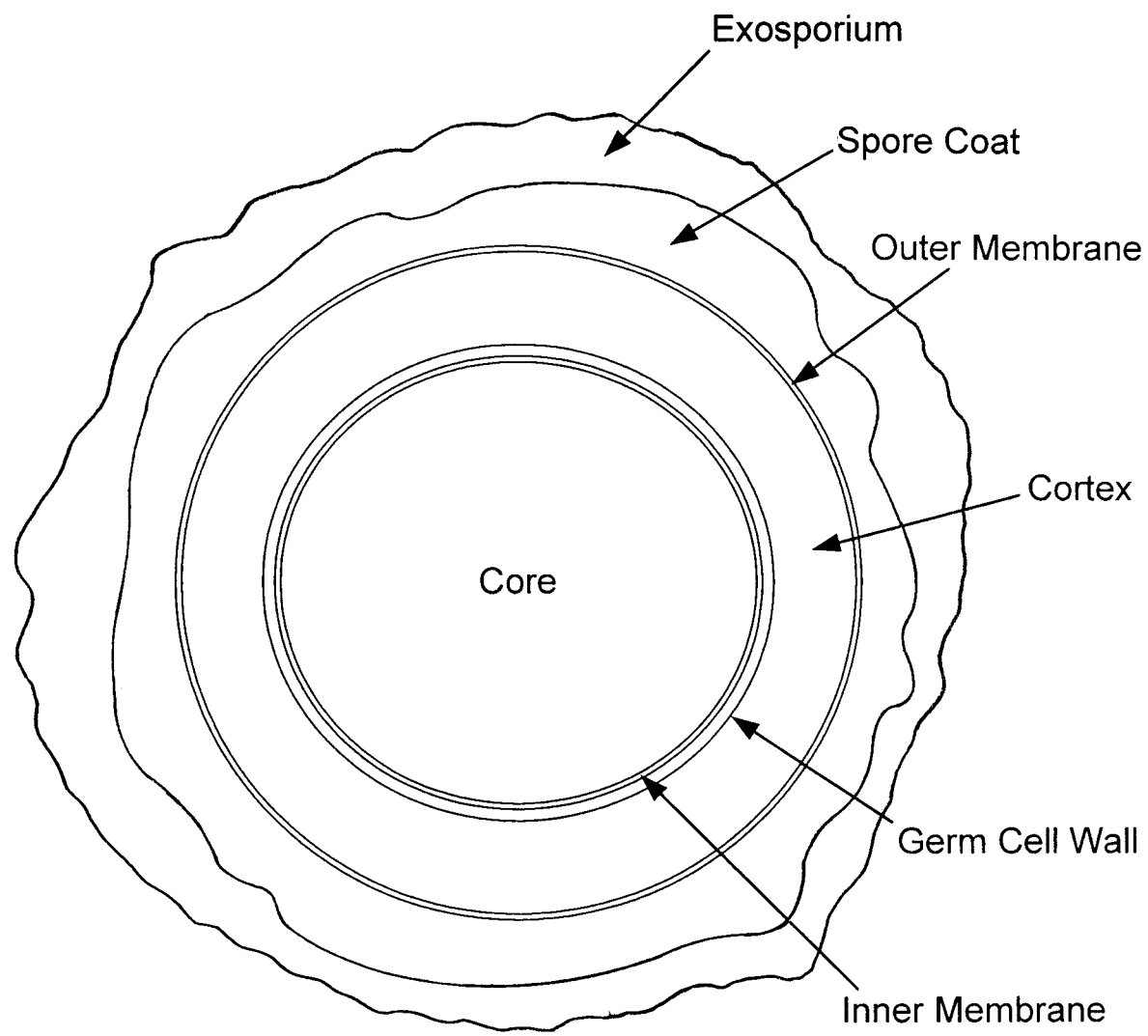

PROCESS AND COMPOSITION FOR KILLING SPORES

TECHNICAL FIELD

This invention relates to a process for killing spores, and to an aqueous composition comprising peracetic acid and hydrogen peroxide that is useful in the process for killing spores.

BACKGROUND

Spores are a highly resistant, dormant cell type formed by some types of bacteria. Endospores (or simply spores) form within the vegetative mother cell in response to adverse changes in the environment, most commonly nutrient depletion.

The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault. Spore forming bacteria cause a number of serious diseases in humans, including botulism, gas gangrene, tetanus, and acute food poisoning. Anthrax results from infection by the aerobic spore form *Bacillus anthracis*.

SUMMARY

Spores are difficult to kill and a problem in the art of sterilization relates to providing an effective process for killing spores. This invention provides a solution to this problem. This invention relates to a process for killing spores and to an aqueous composition for use in the process comprising water, peracetic acid and hydrogen peroxide. The process comprises: contacting the spores with the aqueous composition for a period of time in the range from about 30 seconds to about 20 minutes, or about 30 seconds to about 10 minutes, to effect at least a 4 log, or at least a 5 log, or at least a 6 log reduction in the number of spores capable of reproduction, metabolism and/or growth. The aqueous composition may comprise water and a concentration of peracetic acid in the water in the range from about 0.001 to about 60% by weight, or from about 0.001 to about 30% by weight, or from about 0.001 to about 10% by weight, or from about 0.001 to about 5% by weight, or from about 0.001 to about 2% by weight, or from about 0.001 to about 1% by weight. In a particularly advantageous embodiment, the concentration of peracetic acid in the water may be in the range from about 0.001 to about 0.5% by weight, or from about 0.005 to about 0.4% by weight, or from about 0.01 to about 0.3% by weight, or from about 0.05 to about 0.3% by weight. The weight ratio of peracetic acid to hydrogen peroxide may be in the range from about 0.001 to about 0.5, or from about 0.003 to about 0.4, or from about 0.006 to about 0.3, or from about 0.008 to about 0.2, or from about 0.01 to about 0.1.

BRIEF DESCRIPTION OF THE DRAWINGS

FIG. 1 is a schematic illustration of a bacterial spore that can be killed in accordance with the invention.

DETAILED DESCRIPTION

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "killing" spores refers to rendering the spores incapable of reproduction, metabolism and/or growth.

The term "log reduction" is a mathematical term to show the number of live spores killed by contacting the spores with the aqueous composition of the invention. A "4 log reduction" means that the number of live spores is 10,000 times smaller. A "5 log reduction" means that the number of live spores is 100,000 times smaller. A "6 log reduction" means that the number of live spores is 1,000,000 times smaller.

Sterilization is often taken to refer to a total absence of living spores. Processes that are less rigorous than sterilization may include, for example, disinfection, sanitization, decontamination, cleaning, and the like. The inventive process may be conducted for an effective period of time to achieve at least a 4 log reduction, or at least a 5 log reduction, or at least a 6 log reduction in the number of spores capable of reproduction, metabolism and/or growth. When at least a 6 log reduction is achieved, the process may be referred to as a sterilization process. When a 4 log reduction or a 5 log reduction is achieved, the process may be considered to be less rigorous than a sterilization, but nevertheless useful for various disinfection, sanitization, decontamination and/or cleaning applications.

Bacterial spores typically comprise multiple concentric layers surrounding a central core. This is illustrated in FIG. 1 wherein a bacterial spore is shown which has a central core, inner membrane, germ cell wall, cortex, outer membrane, spore coat and occasionally an exosporium. Oxidizing agents for years have been thought to attack DNA, RNA, protein and most organic matter equally. However, while not wishing to be bound by theory, with the present invention it is believed that the mechanism that is provided involves hydrogen peroxide first piercing holes in multiple layers surrounding the central core of the spores, and then peracetic acid attacking the central core to kill the spores. This mechanism is believed to occur when using aqueous compositions with relatively low concentrations of peracetic acid (e.g., in the range from about 0.001 to about 0.5% by weight), and peracetic acid to hydrogen peroxide weight ratios that are relatively low (e.g., in the range from about 0.001 to about 0.5). Hence, the ratio of peracetic acid to hydrogen peroxide is important with respect to biocidal potentials.

In embodiments wherein the concentration of peracetic acid and hydrogen peroxide is relatively low, for example, peracetic acid concentrations in the range from about 0.001 to about 0.5% by weight, advantages of the inventive process include relatively low costs due to the fact that the concentrations of peracetic acid and hydrogen peroxide used in the process are relatively low in comparison to normal concentrations used in other commercial products using these ingredients. Other advantages of these embodiments include low levels of corrosion of surfaces treated due to the low concentrations of peracetic acid and hydrogen peroxide.

In an embodiment, higher concentrations of the peracetic acid, for example concentrations of peracetic acid up to about 60% by weight, as well as hydrogen peroxide, may be used advantageously when the aqueous composition is applied to spores which are on a substrate. In this embodiment, some of the peracetic acid and hydrogen peroxide may be absorbed and/or neutralized by the substrate. As a result, higher concentrations of peracetic acid and hydrogen peroxide may be required to kill the spores that are on the substrate. With this embodiment, it is believed that the above-indicated mechanism may still apply, but the concentrations of peracetic acid and hydrogen peroxide are increased to account for the fact that when applied to a substrate some of the peracetic acid and/or hydrogen peroxide may be absorbed and/or neutralized by the substrate.

The aqueous composition may comprise water, peracetic acid and hydrogen peroxide, with a concentration of the peracetic acid in the water being in the range from about 0.001 to about 60% by weight, or from about 0.001 to about 30% by weight, or from about 0.001 to about 10% by weight, or from about 0.001 to about 5% by weight, or from about 0.001 to about 2% by weight, or from about 0.001 to about 1% by weight. In a particularly advantageous embodiment, the concentration of peracetic acid in the water may be in the range from about 0.001 to about 0.5% by weight, or from about 0.005 to about 0.4% by weight, or from about 0.01 to about 0.3% by weight, or from about 0.05 to about 0.3% by weight. The weight ratio of peracetic acid to hydrogen peroxide may be in the range from about 0.001 to about 0.5, or from about 0.003 to about 0.4, or from about 0.006 to about 0.3, or from about 0.008 to about 0.2, or from about 0.01 to about 0.1.

The water may comprise tap water, deionized water, distilled water, water purified by osmosis, or a mixture of two or more thereof.

The aqueous composition may further comprise acetic acid, sulfuric acid, or a mixture thereof. The concentration of acetic acid may range up to about 60% by weight, or from about 0.001 to about 60% by weight, or from about 0.001 to about 30% by weight, or from about 0.001 to about 10% by weight, or from about 0.001 to about 5% by weight, or from about 0.001 to about 2% by weight. The concentration of sulfuric acid may range up to about 3% by weight, or from about 0.001 to about 2% by weight. The concentration of each of these may be in the range up to about 1% by weight, or from about 0.001 to about 1% by weight, or from about 0.001 to about 0.5% by weight, or from about 0.001 to about 0.3% by weight.

The aqueous composition may further comprise one or more surfactants to provide the aqueous composition with surface active properties, one or more buffers to provide buffering capability (pH modulation), one or more corrosion inhibitors to provide corrosion inhibiting properties, and/or one or more chelators to provide chelation capacity (water softening).

The surfactant may comprise any compound that lowers surface tension or provides greater wettability. The surfactant may comprise one or more detergent, wetting agents, emulsifiers, foaming agents and/or dispersants. The surfactant may comprise one or more organic compounds that contain both hydrophobic groups and hydrophilic groups. The surfactant may comprise both a water insoluble component and a water soluble component. The surfactant may comprise one or more anionic, cationic, zwitterionic and/or nonionic compounds. The surfactant may comprise one or more alkanolamines, alkylarylsulfonates, amine oxides, poly(oxyalkylene)s, block copolymers comprising alkylene oxide repeat units, carboxylated alcohol ethoxylates, ethoxylated alcohols, alkyl phenols, ethoxylated alkyl phenols, ethoxylated amines, ethoxylated amides, oxiranes, ethoxylated fatty acids, ethoxylated fatty esters, ethoxylated oils, fatty esters, fatty acid amides, glycerol esters, glycol esters, sorbitan, sorbitan esters, imidazolines, lecithin, lignin, glycerides (e.g., mono-, di- and/or triglyceride), olefin sulfonates, phosphate esters, ethoxylated and/or propoxylated fatty acids and/or alcohols, sucrose esters, sulfates and/or alcohols and/or ethoxylated alcohols of fatty esters, sulfonates of dodecyl and/or tridecyl benzenes, sulfosuccinates, dodecyl and/or tridecyl benzene sulfonic acids, mixtures of two or more thereof, and the like. The surfactant may comprise ethanolamine, triethanolamine, octyldimethylamine oxide, nonylphenoxy poly(ethyleneoxy)ethanol, polyalkylene glycol, or a mixture of two or more thereof.

The concentration of the surfactant in the aqueous composition may be in the range up to about 10% by weight, or from about 0.5 to about 10% by weight, or from about 0.5 to about 6% by weight, or from about 1 to about 4% by weight.

The buffer may comprise an alkali metal phosphate, an alkali metal carbonate, or a mixture thereof. The alkali metal may comprise sodium or potassium. The buffer may comprise one or more of monosodium phosphate, disodium phosphate, trisodium phosphate, monopotassium phosphate, dipotassium phosphate, tripotassium phosphate, sodium carbonate, or a mixture of two or more thereof. Disodium phosphate may be used. The concentration of the buffer in the aqueous composition may be in the range up to about 50% by weight, or from about 1% by weight to about 50% by weight, or from about 1% by weight to about 40% by weight, or from about 5% by weight to about 40% by weight, or from about 5% by weight to about 35% by weight.

The corrosion inhibitor may comprise benzotriazole, a sodium salt of benzotriazole, tolyltriazole, a sodium salt of tolyltriazole, or a mixture of two or more thereof. Sodium benzotriazole may be used. A commercially available sodium benzotriazole that may be used is available under the trade designation Cobratec 40S which is believed to be a 40% by weight aqueous solution of sodium benzotriazole. The concentration of the corrosion inhibitor in the aqueous composition may be in the range up to about 10% by weight, or from about 0.01% by weight to about 10% by weight, or from about 0.01% by weight to about 5% by weight.

The chelator may comprise ethylenediaminetetraacetic acid, hydroxyethylidenediphosphonic acid, a sodium salt of either of these acids, or a mixture of two or more thereof. A sodium salt of ethylenediaminetetraacetic acid that may be ethylenediaminetetraacetic acid, tetrasodium salt, tetrahydrate. A commercially available ethylenediaminetetraacetic acid, tetrasodium salt, tetrahydrate that may be used may be available from Akzo Nobel under the trade designation Dissolvine 220-S. Dissolvine 220-S is identified by Akzo Nobel as being a chelating agent containing 83-85% by weight ethylenediaminetetraacetic acid, tetrasodium salt, tetrahydrate. The concentration of the chelator in the aqueous composition may be in the range up to about 50% by weight, or from about 0.01% by weight to about 50% by weight, or from about 0.1% by weight to about 30% by weight.

The aqueous composition may further comprise one or more fragrances, dyes, mixtures thereof, and the like.

The inventive process may comprise contacting spores with the aqueous composition for a period of time in the range from about 30 seconds to about 20 minutes, or from about 30 seconds to about 10 minutes, to provide for the desired level of reduction (e.g., at least a 4 log reduction, or at least a 5 log reduction, or at least a 6 log reduction) in the number of living spores. When contacted, the spores may be on a substrate. The substrate may be made of any material including brass, copper, aluminum, stainless steel, carbon steel, rubber, plastic, glass, wood, painted surface, or a combination of two or more thereof. The substrate may comprise a table top, counter top, floor, wall, ceiling, window, door, door handle, sink, faucet, toilet, toilet seat, and the like. The substrate may comprise a medical, dental, pharmaceutical, veterinary or mortuary device. The substrate may comprise human skin.

The temperature of the aqueous composition when applied to the substrate may be in the range from about 10° C. to about 70° C., or from about 20° C. to about 60° C., or from about 25° C. to about 55° C., or from about 30° C. to about 50° C. The aqueous composition may be applied using any standard technique including spraying, brushing, dipping, and the like.

The spores that may be treated (i.e., killed) include bacterial spores. The spores may comprise bacteria of the *Bacillus* or *Clostridia* genera. The spores may comprise *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans, Bacillus anthracis*, or a mixture of two or more thereof. The spores may comprise one or more *Bacillus subtilis* strains and/or wild type *Bacillus subtilis* spores.

Examples

The efficacy of the inventive process is assessed using a time kill suspension test method and spores of *Bacillus subtilis.*

Peracetic acid (PAA) and hydrogen peroxide ($H_2O_2$) are prepared as concentrated stocks (3× concentrate). Each test contains 100 µl of the PAA concentrate and 100 µl of the $H_2O_2$ concentrate. Controls containing only PAA or $H_2O_2$ are also prepared. These contain 100 µl of either the PAA concentrate or $H_2O_2$ concentrate and 100 µl of de-ionized water. To each test, 100 µl of spores are added while starting the timer concurrently. The samples are mixed thoroughly. At the appropriate contact times, 10 µl of the appropriate test sample are placed into 90 µl of the appropriate neutralizing solution, mixed thoroughly and incubated for at least 10 minutes. Ten fold serial dilutions are prepared through $10^{-6}$ and plated using the drop counting method. Plates are incubated aerobically at 37° C. for 1-2 days. Following incubation, colony forming units (CFU) are counted using standard plate count techniques and converted to log 10 values for analysis.

The results are indicated in the tables below.

TABLE 1

Time (min) to achieve 4 log reduction for various PAA/$H_2O_2$ combinations (calculated from curves fitted to time/kill data)

| | | | | | | | | |
|---|---|---|---|---|---|---|---|---|
| $H_2O_2$ concentration (%) | 6.40 | 48.64 | 15.68 | 7.2 | 7.36 | 3.67 | 2.14 | 1.36 |
| (% by weight) | 3.20 | 97.28 | 15.68 | 13.12 | 8.24 | 3.92 | 2.28 | 1.68 |
| | 1.60 | 168.96 | 28.16 | 24.32 | 14.08 | 4.64 | 3.52 | 1.82 |
| | 0.80 | 343.04 | 33.7 | 32.96 | 19.36 | 7.6 | 3.96 | 1.9 |
| | 0.40 | 639.34 | 92.16 | 69.12 | 43.52 | 14.08 | 6.4 | 2.08 |
| | 0.20 | 1213.99 | 286.72 | 209.12 | 92.16 | 32 | 11.92 | 2.22 |
| | 0.10 | 2305.13 | — | — | 337.92 | 54.4 | 19.36 | 3.28 |
| | 0.00 | — | 711625 | 67744.68 | 6449.101 | 613.9362 | 70.40 | 4.64 |

TABLE 1-continued

Time (min) to achieve 4 log reduction for various PAA/H$_2$O$_2$ combinations
(calculated from curves fitted to time/kill data)

|  | 0.00 | 0.005 | 0.01 | 0.02 | 0.04 | 0.08 | 0.16 |
|---|---|---|---|---|---|---|---|
|  |  |  | PAA concentration (% by weight) |  |  |  |  |

TABLE 2

PAA kill time divided by PAA/H$_2$O$_2$ kill time from values in table 1 (i.e.
Potentation of PAA activity in the presence of H$_2$O$_2$)

| H$_2$O$_2$ concentration (% by weight) | 6.40 | — | 45384.25 | 9408.98 | 876.24 | 167.29 | 32.90 | 3.41 |
|---|---|---|---|---|---|---|---|---|
|  | 3.20 | — | 45384.25 | 5163.47 | 782.66 | 156.62 | 30.88 | 2.76 |
|  | 1.60 | — | 25270.77 | 2785.55 | 458.03 | 132.31 | 20.00 | 2.55 |
|  | 0.80 | — | 21116.47 | 2055.36 | 333.11 | 80.78 | 17.78 | 2.44 |
|  | 0.40 | — | 7721.63 | 980.10 | 148.19 | 43.60 | 11.00 | 2.23 |
|  | 0.20 | — | 2481.95 | 323.95 | 69.98 | 19.19 | 5.91 | 2.09 |
|  | 0.10 | — | — | — | 19.08 | 11.29 | 3.64 | 1.41 |
|  |  | 0.00 | 0.005 | 0.01 | 0.02 | 0.04 | 0.08 | 0.16 |
|  |  |  |  | PAA concentration (% by weight) |  |  |  |  |

TABLE 3

H$_2$O$_2$ kill time divided by PAA/H$_2$O$_2$ kill time from values in table 1
(i.e. Potentation of H$_2$O$_2$ activity in the presence of PAA)

| H$_2$O$_2$ concentration (% by weight) | 6.40 | — | 3.10 | 6.76 | 6.61 | 13.25 | 22.73 | 35.76 |
|---|---|---|---|---|---|---|---|---|
|  | 3.20 | — | 6.20 | 7.41 | 11.81 | 24.82 | 42.67 | 57.90 |
|  | 1.60 | — | 6.00 | 6.95 | 12.00 | 36.41 | 48.00 | 92.84 |
|  | 0.80 | — | 10.18 | 10.41 | 17.72 | 45.14 | 86.63 | 180.55 |
|  | 0.40 | — | 6.94 | 9.25 | 14.69 | 45.41 | 99.90 | 307.38 |
|  | 0.20 | — | 4.23 | 5.81 | 13.17 | 37.94 | 101.84 | 546.84 |
|  | 0.10 | — | — | — | 6.82 | 42.37 | 119.07 | 702.78 |
|  |  | 0.00 | 0.005 | 0.01 | 0.02 | 0.04 | 0.08 | 0.16 |
|  |  |  |  | PAA concentration (% by weight) |  |  |  |  |

The values shown in Table 1 represent the time taken (minutes) to achieve a 4 log reduction in spore count in the presence of either PAA or H$_2$O$_2$ alone, or in combination with each other. For PAA concentrations 0.005, 0.01, 0.02 and 0.04% (in the absence of H$_2$O$_2$), the values shown are extrapolated based on the experimental data obtained for PAA concentrations 0.08, 0.16 and 0.32%. Similarly, for H$_2$O$_2$ concentrations 0.1, 0.2 and 0.4% (in the absence of PAA), the values shown are extrapolated from experimental data. All other values are generated from spore kill data.

Table 2 illustrates the potentation of spore killing by PAA when in the presence of H$_2$O$_2$. At higher PAA concentrations (0.08 and 0.16% PAA) relatively little activity is gained by the addition of even very high concentrations of H$_2$O$_2$. For example, 0.16% PAA is only 3.41 times more active in the presence of 6.4% H$_2$O$_2$, as compared to the activity of 0.16% PAA alone.

However, as the concentration of PAA is reduced, the effect of adding H$_2$O$_2$ becomes more dramatic, with PAA spore killing activity being hundreds, thousands and even tens of thousands of times greater when in the presence of low concentrations of H$_2$O$_2$. For example, 0.02% PAA is 333.11 times more active in combination with 0.8% H$_2$O$_2$ than when used alone.

Table 3 illustrates the potentation of spore killing by H$_2$O$_2$ when in the presence of PAA. The enhancement of the spore killing activity of H$_2$O$_2$ when in the presence of PAA is far less pronounced, with relative improvement in the spore killing activity of H$_2$O$_2$ in combination with all but the highest concentrations of PAA being no greater than about 100 times.

While the invention has been explained in relation to various embodiments, it is to be understood that modifications thereof may become apparent to those skilled in the art upon reading the specification. Therefore, it is to be understood that the scope of the invention specified herein is intended to include all modifications that may fall within the scope of the appended claims.

The invention claimed is:

1. A process for killing *Bacillus subtilis* bacterial spores, comprising: contacting the spores with an aqueous composition comprising water, peracetic acid, acetic acid, hydrogen peroxide, and sulfuric acid for 10 to 20 minutes to effect at least a 4 log reduction in the number of spores capable of reproduction, metabolism and/or growth, the aqueous composition having a concentration of peracetic acid in the range from 0.02 to 0.08% by weight,
the concentration of hydrogen peroxide being in the range from 0.4 to 0.8% by weight,
the weight ratio of peracetic acid to hydrogen peroxide being in the range from 0.025 to 0.2, and the temperature of the aqueous composition being in the range from about 10° C. to about 70° C.

2. The process of claim 1 wherein the temperature of the aqueous composition is in the range from about 20° C. to about 60° C.

3. The process of claim 1 wherein the concentration of acetic acid in the aqueous composition is in the range from 0.001 to 5% by weight.

4. The process of claim 1 wherein the concentration of sulfuric acid in the aqueous composition is in the range from 0.001 to 2% by weight.

5. The process of claim 1 wherein the spores are on a substrate and the substrate comprises a medical, dental, pharmaceutical, veterinary or mortuary device, wherein the device is made of a material comprising brass, copper, aluminum, steel, or a combination of two or more thereof.

* * * * *